United States Patent [19]

MaCovski

[11] 4,107,532
[45] Aug. 15, 1978

[54] ORTHOGONAL SCAN COMPUTERIZED TOMOGRAPHY

[75] Inventor: Albert MaCovski, Palo Alto, Calif.

[73] Assignee: The Board of Trustees of the Leland Stanford Junior University, Stanford, Calif.

[21] Appl. No.: 741,127

[22] Filed: Nov. 11, 1976

[51] Int. Cl.[2] .................. A61B 6/02; G01N 23/08
[52] U.S. Cl. ............................. 250/360; 250/445 T
[58] Field of Search ............... 250/445 T, 524, 224, 250/313, 314, 360

[56] References Cited

U.S. PATENT DOCUMENTS 2,512,242  6/1950  De Lassaus St. Genies ... 250/445 T
3,588,480  6/1971  Unger et al. ........................ 250/224

FOREIGN PATENT DOCUMENTS 808,157  1/1959  United Kingdom .................. 250/313

Primary Examiner—Alfred E. Smith
Assistant Examiner—T. N. Grigsby

[57] ABSTRACT

Two sources, each producing divergent beams of radiation, are translated in orthogonal directions. The divergent beams are each scanned through the object being studied. The sum of the angular extent of each of the divergent beams is approximately 180° so that the detected radiation transmitted through the object provides all of the information required to produce a cross-sectional image of the object. An advantage in the use of the orthogonal scans of the present invention is that faster scan times are achieved due to the simple translational motion required of each of the two sources. This allows studies to be made of dynamic organs such as the heart. A further advantage is that the detectors used can be simply calibrated during the scan since, for part of the scan, the divergent beam is not transmitted through the object.

24 Claims, 4 Drawing Figures

ORTHOGONAL SCAN COMPUTERIZED TOMOGRAPHY

The invention described herein was made in the course of work under a grant from the Department of Health, Education, and Welfare.

BACKGROUND OF THE INVENTION

1. Field of the Invention

This invention relates to computerized tomography imaging systems. In a primary application the invention relates to rapidly obtaining cross-sectional X-ray images so that moving organs can be studied.

2. Description of Prior Art

The instrumentation presently used in computerized tomography falls into two general categories. The first is a two-motion system where all of the projections required to reconstruct a cross-sectional image are obtained by a combination of linear and orbital scanning. At each angular position of the source with respect to the object a linear traverse is made. This is repeated at many angular positions until a complete set of projections are obtained. This two motion procedure is described in U.S. Pat. No. 3,778,614 issued Dec. 11, 1973.

The second general category employs angular or orbital motion only. A fan beam of radiation, including X-rays or gamma rays, is transmitted through the object. Both the X-ray source and fan-beam detector are rotated around the body so as to produce projection data over the full range of angles. This data is then used to provide a cross-sectional reconstruction of the object. Such a fan-beam computerized tomographic apparatus is disclosed and claimed in U.S. Pat. applications Ser. Nos. 528,024; 528,025; and 528,026 all filed Nov. 29, 1974 and assigned to the same assignee as the present invention.

Each of the two scanning systems described is unsuitable for the study of rapidly moving organs, such as the heart, because of the relatively long scan time. The second scanning system, employing oribital motion only, provides scans of approximately five seconds. This time is suitable for respiratory studies since it is within a normal breath-holding interval. Five seconds, however, is unsuitable for studying the cardiac or digestive organs where more rapid motions are involved. In addition, this second scanning system is subject to distorting artifacts since the detectors are not calibrated while a patient is being scanned.

SUMMARY OF THE INVENTION

An object of the invention is to provide apparatus for obtaining cross-sectional 3D tomographic images of an object where the required data is acquired in a relatively short period of time. A further object of this invention is to provide detector calibration information while the object is being scanned.

Briefly in accordance with the invention two sources are used having divergent beams directed at an object in orthogonal directions. The sources are simultaneously translated in orthogonal paths with each of their divergent beams scanning the object. The radiation transmitted through the object is detected and provides a complete set of projection data over approximately 180°. This data is used to reconstruct a 3D tomographic image of the object. The radiation reaching the detectors directly, without passing through the object, is used to calibrate the detectors.

BRIEF DESCRIPTION OF THE DRAWINGS

For a more complete disclosure of the invention, reference may be made to the following detailed description of several illustrative embodiments thereof which is given in conjunction with the accompanying drawings, of which.

DESCRIPTION OF THE PREFERRED EMBODIMENT

Figure 1:
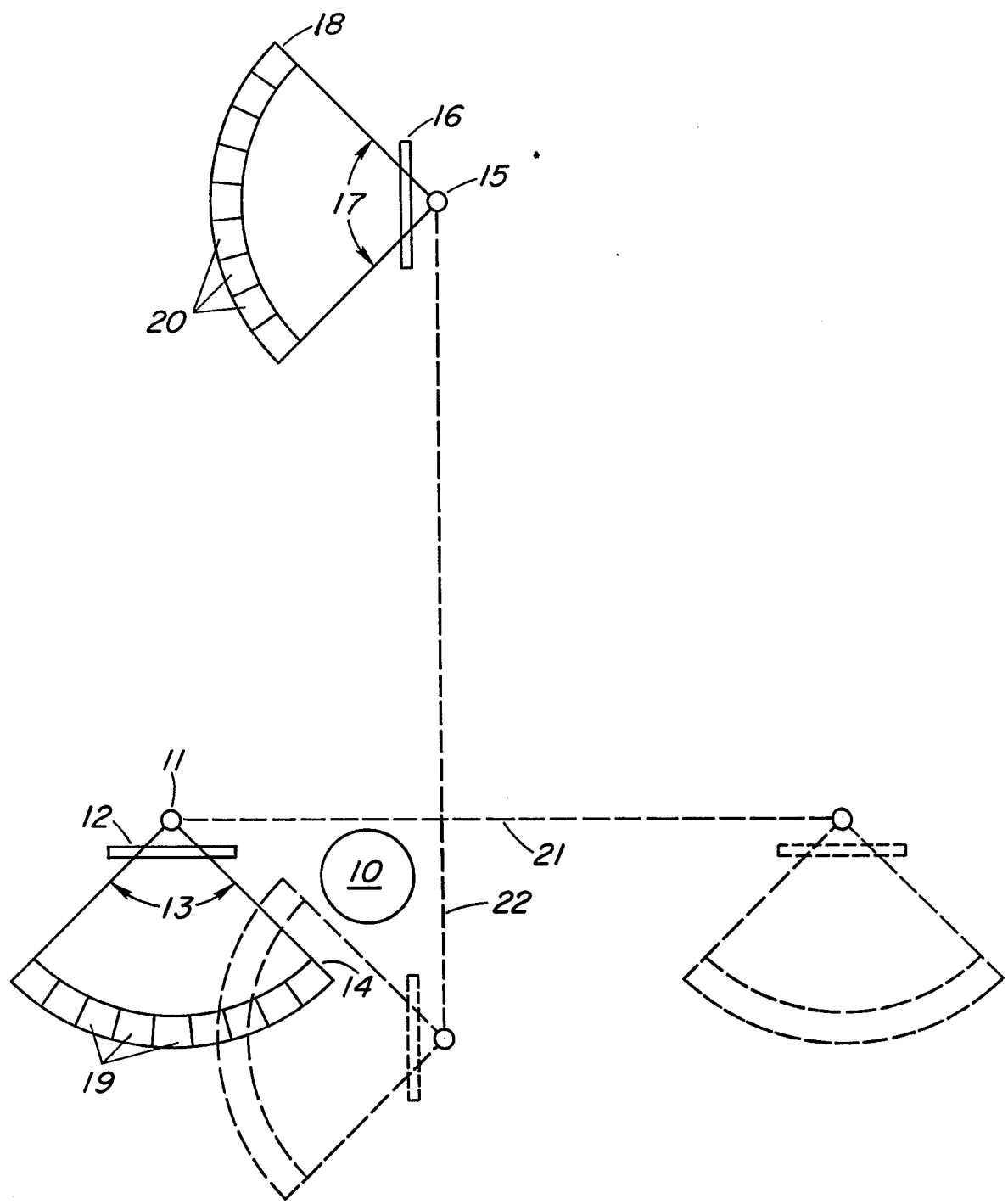
FIG. 1 is a schematic representation of an embodiment of the invention using translating detectors.

An understanding of the broad aspects of the invention may best be had by reference to FIG. 1 of the drawings. It is desired to make a cross-sectional image or 3D tomographic image of object 10. In most applications the object will be a region of the body such as the head or abdomen. As has been widely reported, a cross-sectional image can be reconstructed from a complete set of projections made over 180°. In FIG. 1 these projections are obtained by scanning two divergent fan-shaped beams 13 and 17, through object 10.

The divergent fan-shaped beams are formed from x-ray sources 11 and 15 which, in general, will be X-ray tubes. These could also represent a variety of other high energy X-ray or gamma ray sources such as radioactive isotopes. The radiation from each source is collimated into a planar fan beam using collimators 12 and 16. These are normally absorbing metals, such as lead, with a slot defining the fan-shaped beams 13 and 17. Since projections are desired over 180°, the sum of the angular extent of each fan beam 13 and 17 should be at least 180°. A preferred arrangement is the symmetrical one where each fan angle is approximately 90°. If the sum of the fan angles is less than 180° reconstruction methods can be used, which will subsequently be discussed, which provide a reconstruction with incomplete data.

Source 11 is translated horizontally along path 21 and source 15 is translated vertically along path 22 with each of the fan beams, 13 and 17, scanned completely through object 10. The transmitted radiation is detected by detector arrays 14 and 18. These can be arrays of X-ray scintillation crystals, such as sodium iodide, followed by photomultipliers which detect the resultant light scintillations and produce electrical signals 19 and 20. Alternatively these detector arrays can be gaseous detectors using a gas such as Xenon. A detector array of this type is disclosed and claimed in U.S. Pat. application No. 528,025, filed Nov. 29, 1974, and assigned to the same assignee as the present invention.

As shown in FIG. 1, it may prove necessary to start the translation of source 15 at a point further away from object 10 than that of source 11 to avoid conflict between the two translating structures. As is shown in FIG. 1, source 11 and its detector array 14 will avoid source 15 and detector array 20 because the former begin their translation closer to object 10. The source translation paths shown in FIG. 1 are each rectilinear. A slightly curved path may also be used. A curved path can increase the effective range of angles of the projection data and thus partially compensate for a somewhat reduced fan angle from each source. In any case the radius of curvature of the curved path is considerably greater than the distance from the source to the center of the object 10. Existing rotary fan beam scanners employing orbital motion only have the source traversing a circular path whose radius of curvature is approximately equal to the distance from the source to the center of the object.

One of the problems with rotary fan beam scanners employing solely orbital motion is the inability to calibrate the detector elements. Various detectors have different degrees of drift in their sensitivity. In the rotary fan beam scanner the beam is always transmitted through the object, so that a calibration cannot be accomplished while the scan is in progress. In these systems a very slight drift in a detector element results in serious artifacts in the reconstructed image. This problem is overcome in the scanner built by American Science and Engineering of Cambridge, Massachusetts by utilizing a complete circular ring of 600 detectors. This system is thus quite complex, and has the previously referred to problem of limited scanning speed. In the system of FIG. 1 the calibration is readily accomplished while the patient, object 10, is being scanned. Both divergent fan beams, 13 and 17, during some portion of the traverse, are transmitted directly to detector arrays 14 and 18 without going through object 10. During these portions of the traverse, corresponding to either the beginning or end of the scanning interval, the radiation is measured by the detectors and used as a calibration. It is assumed that the sources 11 and 15 have known outputs at all times. This is either accomplished using very stable sources or using additional source-monitoring detectors, not shown, to calibrate the output of the sources.

The electrical signals 19 and 20 represent the outputs of detector arrays 14 and 18. These signals are applied to a computer, in the conventional fashion, to provide a reconstructed cross-sectional image of object 10. The output of each detector element, as it is scanned, represents a projection at a specific angle. It is typical to provide projection data at increments of approximately one degree. Thus detector arrays 14 and 18 will typically each have approximately 90 elements at one degree increments. The computer can reconstruct the cross-sectional image from the projection data using either iterative or direct methods. A general discussion of these techniques is given in the paper, "Three Methods for Reconstructing Objects From X-Rays: A Comparative Study," by G. T. Herman and S. W. Rowland in *Computer Graphics and Image Processing*, Vol. 2, 1973, pp. 151–178.

In the iterative reconstruction method the resultant image is compared with the measured projection data and altered until a good fit is obtained. As such this method is applicable for the case of incomplete data where projections are available over less than 180°. This would be the case if the sum of the fan angles of divergent beams 13 and 17 were less than 180°.

Figure 2:
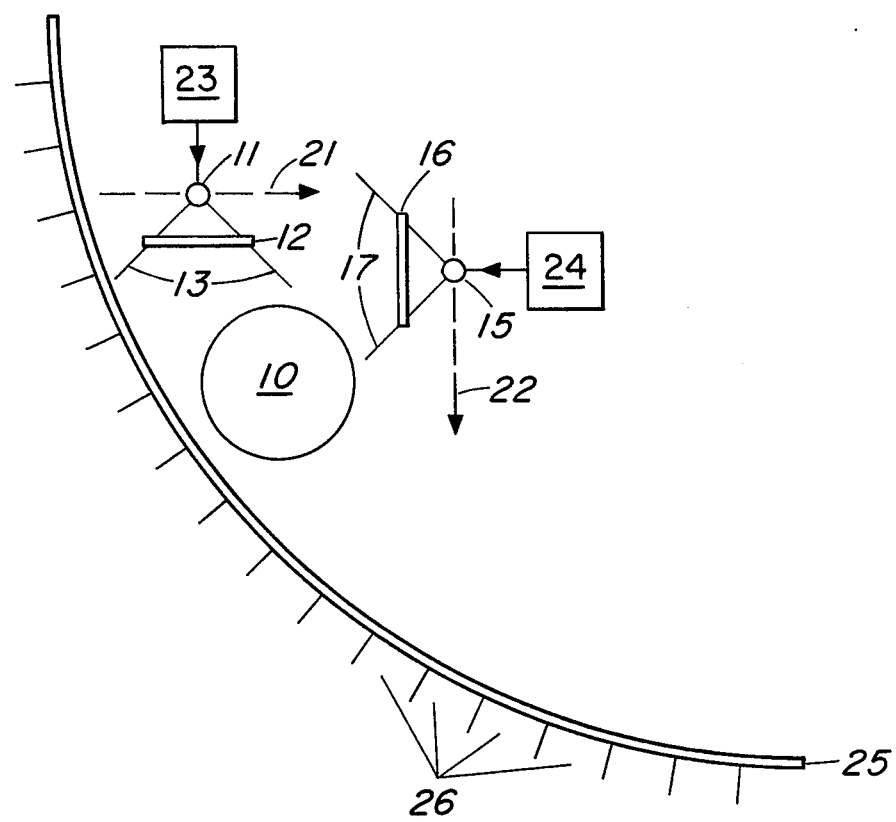
FIG. 2 is a schematic representation of an embodiment of the invention using a fixed detector system.

In the system described in FIG. 1 the detector arrays 14 and 18 were traversed in synchronism with the sources 11 and 15. In a system employing very rapid scanning, such as for studies of the heart, it is important to minimize the inertia of the moving system. FIG. 2 shows a system using a fixed detector array 25, thus requiring source motion only to facilitate rapid scanning. As in FIG. 1 X-ray sources 11 and 15 are collimated using fan collimators 12 and 16 to produce divergent fan beams 13 and 17 respectively. These sources are again traversed along paths 21 and 22. The detector array 25 is now a fixed array of detector elements which receives radiation from both fan beams 13 and 17. The detector array 25 is curved so that the rays from both traversing fan beams will intersect the detector at an angle which does not depart excessively from normal incidence. This could also be accomplished by a right angle structure using a vertical and horizontal array joined at the corner.

In order to distinguish which detector output represents which source radiation, the sources 11 and 15 can be alternately pulsed. This does not reduce their power output capabilities since they are heat dissipation limited so that their average power can remain the same as that of continuous operation. Pulsers 23 and 24 are used to control the outputs of sources 11 and 15. This is usually accomplished by using grid-controlled X-ray tubes. Alternatively, however, the high voltage supply could be pulsed. The detector output signals 26 consist of pulses which alternately represent the detected radiation from source 11 and source 15. These detector output signals can be appropriately gated and applied to the reconstruction computer.

The reconstruction systems, as with FIG. 1, are the classical ones involving cross-sectional reconstruction from projections. In the moving detector system of FIG. 1 the signal from each detector element represented a projection at a specific angle. This is not the case in FIG. 2 because of the stationary detector. The information representing each projection angle, in this case, is a ray of a given angle scanning along the detector array. Thus when the detector signals 26 are stored in a computer they can be reordered to represent parallel sets of rays at each projection angle. This reordering procedure is similar to the one described in the aforecited U.S. Patent applications Ser. Nos. 528,024–026. However, since the system of FIG. 2 uses a translating fan beam, the reordering procedure is more straightforward.

Figure 3:
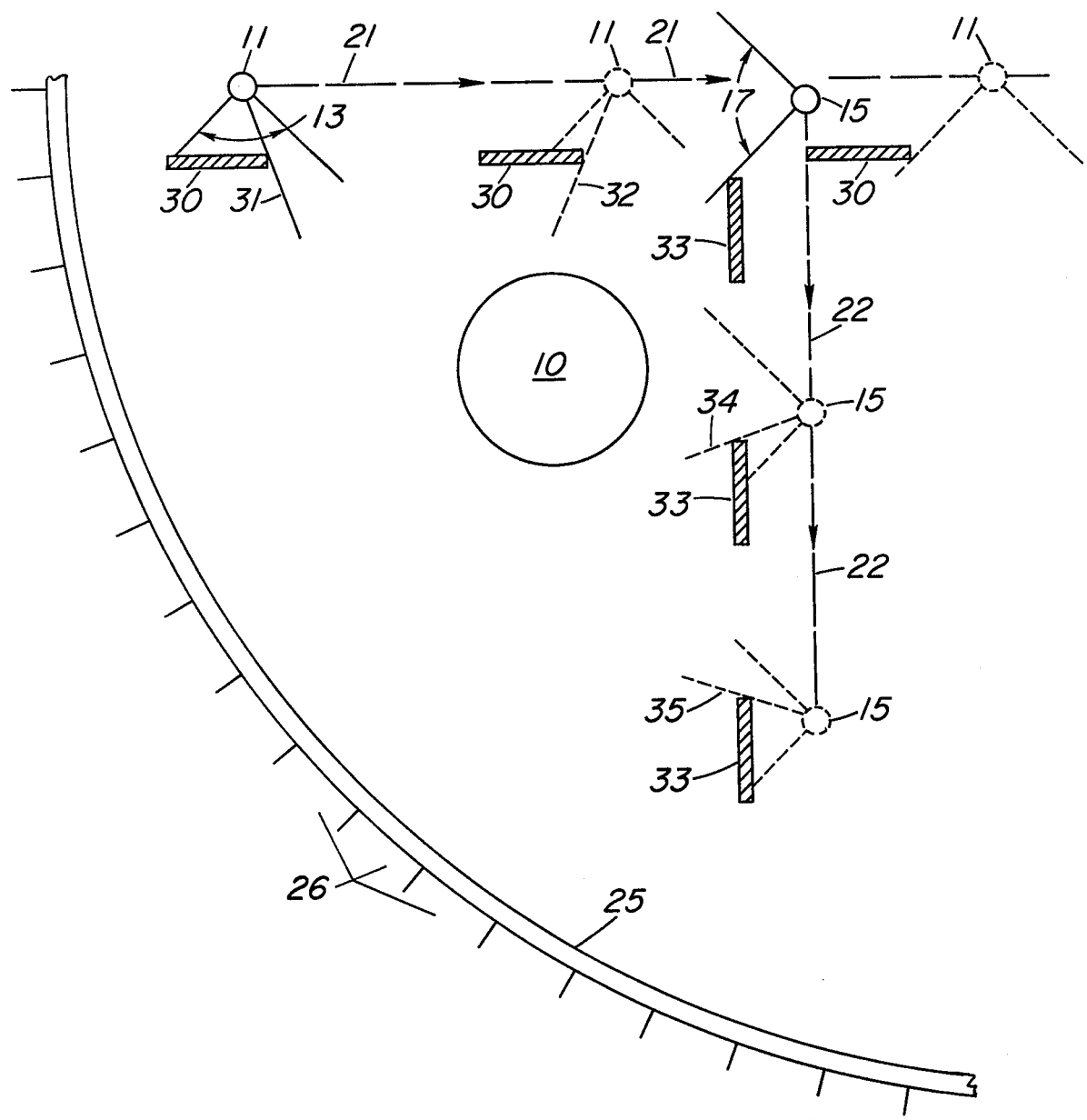
FIG. 3 is a schematic representation of a fixed detector system using a moving obscurer to avoid overlap of the two beams.

FIG. 3 illustrates another embodiment of the fixed detector system which avoids the requirement of pulsing the sources 11 and 15. A method of controlled shielding is used to insure that each detector element, at any portion of the scan, represents radiation from only one of the two sources. As shown a moving obscurer 30 partially obscures divergent beam 13 emanating from source 11. Similarly moving obscurer 33 partially obscures divergent beam 17 emanating from source 15. These obscurers each move with respect to the sources during the traverse. In general, a portion of each divergent beam, which does not get transmitted through the object, is obscured to avoid overlap of the two divergent beams at the detector. At the beginning of the traverse, with source 11 at the left and source 15 at the top, obscurer 30 blocks part of divergent beam 13. Ray 31, which intersects detector array 25 at the highest point of the rays from source 11, intersects the detector array at a point below that of the lowest ray from source 15. A similar situation exists at the end of the traverse where source 11 is at the right and source 15 is at the bottom. Here ray 35 from source 15, which intersects detector array 25 at the lowest point of the rays from source 15, intersects the detector array at a point above that of any of the rays from source 11. The closest situation exists in the center of the traverse where the system is designed so that ray 32 from source 11 intersects the detector array at a lower point than that of ray 34 from source 15.

Thus, using the moving obscurer to block unused rays, a portion of the detector output signals 26 can be assigned to source 11 and another portion to source 15. In this way the projection data are separated without requiring pulsing. It is important to note, however, that the self-calibrating feature of this system has not been lost. When source 11 is on the right, at the end of the traverse, the entire divergent fan beam is not obscured and is not transmitted through object 10 so that it can be measured for calibration. Similaly, when source 15 is at the top, at the beginning of the traverse, it has an unobscured divergent fan beam which is used for calibration.

Figure 4:
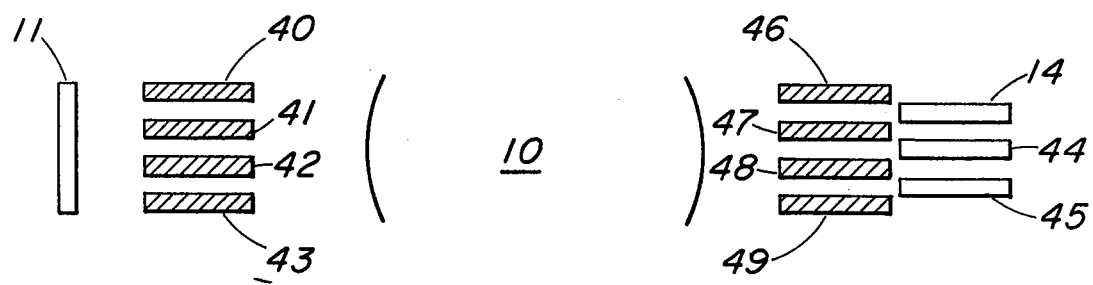
FIG. 4 is a schematic representation of an embodiment of the invention for scanning multiple sections.

In the systems discussed thusfar a single planar cross section was imaged during each traverse. FIG. 4 illustrates a method of simultaneously acquiring the data for a number of sections. This aspect of the present present invention is similar to the EMI head scanner which simultaneously acquires the data for two adjacent sections. Only one source-detector system is shown since the two are essentially identical. Source 11, as shown, is an elongated line source. This is achieved by forming an elongated shaped electron beam in the X-ray tube which then impinges on a moving or stationary target. The radiation from source 11 is collimated into an array of planar fan beams. As an example, FIG. 4 shows the collimation into three fan beams using collimators 40, 41, 42, and 43. On the detector side FIG. 4 shows the cross section of detector arrays 14, 44, and 45. These can either be moving detector arrays, as in FIG. 1, or fixed detector arrays, as in FIGS. 2 and 3. The radiation coming out of object 10 is again collimated into three fan beams using collimators 46, 47, 48, and 49. These are helpful in preventing the scattered radiation generated in object 10 from reaching the detectors. The outputs from each of these detectors are applied to computers for reconstruction as previously described. In this way a volume of object 10, consisting of any array of parallel planes, is simultaneously scanned. This is important in dynamic cardiac studies so as to accurately observe the relative motions of different portions of the heart.

A volume can also be scanned using the conventional point-like sources of FIGS. 1, 2, and 3 without requiring the elongated source of FIG. 4. For example in FIG. 1 the slot in fan beam collimators 12 and 16 can be widened to generate a thicker divergent beam which can include a number of planar sections. Detectors 14 and 18 then become multiple detector arrays which simultaneously acquire the data for a few planes. Although the planes are not parallel, because they each emanate from point X-ray sources 11 and 15, for relatively small objects 10, the planes will be approximately parallel as they pass through the object. In that case the reconstruction systems previously described can be used to reconstruct each plane in the volume being scanned with negligible errors. If, however, the various planes have appreciable relative angles with each other, and pass through a relatively large object, this must be considered in the reconstruction process. The outer skewed fan-beam planes from sources 11 and 15 will not coincide in the same plane so that the previously described reconstruction systems may present significant errors if an array of parallel planes are assumed. A geometric configuration of this type can be reconstructed using a fairly complex three-dimensional iterative procedure. Such a procedure is described in the Proceedings of the Second International Conference on Roentgendensitometry entitled, "Algorithm for Dynamic Spatial Reconstruction," by G. T. Herman, April, 1976.

Although the primary applications of these orthogonal scanning systems use high energy radiation including X-rays and gamma rays, other types of radiation can also be used such as ultrasound and light.

What is claimed is:

1. In a method of computerized tomography the steps of:
    directing divergent beams of radiation from two sources in orthogonal directions through an object;
    translating each source in orthogonal paths such that each divergent beam is scanned across the lateral extent of the region of the object being examined;
    detecting the radiation that is transmitted through the object at each of a plurality of positions within the angle subtended by each of the divergent beams at each source position to derive projection data representing substantially all angles required to produce a reconstruction; and
    reconstructing a 3-D tomographic image of the object from the projection data.

2. The method of claim 1 wherein the sums of the angles subtended by each of the divergent beams, in the plane of the paths of the sources, is substantially 180°.

3. The method of claim 2 wherein the angle subtended by each of the divergent beams is 90°.

4. The method of claim 1 wherein the divergent beams are each planar fan beams which are detected by line arrays of detector elements which intercept the fan beams that are transmitted through the object.

5. The method of claim 1 wherein the divergent beams each include a plurality of planar fan beams each of which is detected by a line array of detector elements which intercept the planar fan beam that is transmitted through the object.

6. The method of claim 1 wherein each source is translated over orthogonal paths consisting of rectilinear motion at 90° with respect to the translation of the other source.

7. The method of claim 1 wherein each source is translated over an orthogonal path consisting of an arc of a circle whose radius of curvature is substantially larger than the distance from the source to the center of the object.

8. The method of claim 1 wherein the step of detecting the transmitted radiation includes two detector arrays which are translated in registration with the translation of the sources.

9. The method of claim 1 wherein the step of detecting the transmitted radiation includes detectors which remain fixed during the translation of the sources.

10. The method of claim 9 wherein a single detector array detects the transmitted radiation from both sources, said method further including the step of alternately pulsing the two sources whereby the radiation from each source can be distinguished by the time of detection thereof.

11. The method of claim 9 wherein a single detector array detects the transmitted radiation from both sources; said method further including the step of moving an obscurer associated with each X-ray source to partially block each of the divergent beams during their translation such that each element of the detector receives transmitted radiation from only one of the sources at any time.

12. The method of claim 1 further including the step of calibrating the detectors by detecting the radiation of each of the divergent beams at portions of the paths of the sources where the beams are not transmitted through the object.

13. Apparatus for producing a 3-D tomographic image of an object comprising:
two source means each producing a divergent beam of radiation in orthogonal directions;
means for translating each source in orthogonal paths such that each divergent beam is scanned across the lateral extent of the region of the object being examined;
detector means for detecting the radiation transmitted through the object at each of a plurality of positions within the angle subtended by each of the divergent beams at each source position to produce an array of projection signals; and
means for reconstructing a 3-D tomographic image of the object from the projection signals.

14. Apparatus as recited in claim 13 wherein the sum of the angles subtended by each of the divergent beams, in the plane of the paths of the sources, is substantially 180°.

15. Apparatus as recited in claim 14 wherein the angle subtended by each of the divergent beams is substantially 90°.

16. Apparatus as recited in claim 13 wherein the divergent beams are each planar fan beams and the detector means are line arrays of detector elements which intercept the fan beams that are transmitted through the object.

17. Apparatus as recited in claim 13 wherein the divergent beam each include a plurality of planar fan beams and the detector means includes a plurality of line arrays of detector elements which intercept the planar fan beams that are transmitted through the object.

18. Apparatus as recited in claim 13 wherein the orthogonal paths are rectilinear paths at 90° to each other.

19. Apparatus as recited in claim 13 wherein the orthogonal paths are arcs of circular paths where the radii of curvature are substantially greater than the distance from each source to the center of the object.

20. Apparatus as recited in claim 13 wherein the detector means includes two detector arrays which are translated in registration with the paths of the sources.

21. Apparatus as recited in claim 13 wherein the detector means includes detectors which remain fixed during the translation of the sources.

22. Apparatus as recited in claim 21 wherein a single detector array detects the transmitted radiation from both sources, said apparatus further including means for alternately pulsing the two souces whereby the radiation from each source can be distinguished by the time of detection thereof.

23. Apparatus as recited in claim 21 wherein a single detector array detects the transmitted radiation from both sources, said apparatus further including a moving obscurer associated with each X-ray source which partially blocks the divergent beam during its translation such that each element of the detector receives transmitted radiation from only one of the sources at a time.

24. Apparatus as recited in claim 13 further including means for calabrating the detectors by detecting the radiation of each of the divergent beams at portions of the paths of the sources where the beams are not transmitted through the object.

* * * * *